(12) United States Patent
Long

(10) Patent No.: US 11,337,730 B2
(45) Date of Patent: May 24, 2022

(54) VAGINAL SPECULUM

(71) Applicant: Kaohsiung Medical University, Kaohsiung (TW)

(72) Inventor: Cheng-Yu Long, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 189 days.

(21) Appl. No.: 16/790,245

(22) Filed: Feb. 13, 2020

(65) Prior Publication Data
US 2020/0261116 A1    Aug. 20, 2020

Related U.S. Application Data

(60) Provisional application No. 62/805,996, filed on Feb. 15, 2019.

(51) Int. Cl.
*A61B 17/42* (2006.01)
*A61B 17/02* (2006.01)
*A61B 17/00* (2006.01)

(52) U.S. Cl.
CPC .......... *A61B 17/42* (2013.01); *A61B 17/0206* (2013.01); *A61B 17/0218* (2013.01); *A61B 2017/00477* (2013.01); *A61B 2017/00862* (2013.01)

(58) Field of Classification Search
CPC . A61B 17/42; A61B 17/0206; A61B 17/0218; A61B 17/0293; A61B 2017/00862
See application file for complete search history.

(56) References Cited

U.S. PATENT DOCUMENTS

| | | | |
|---|---|---|---|
| 8,118,738 B2* | 2/2012 | Larkin | A61B 1/32 600/222 |
| 8,690,767 B2* | 4/2014 | Kecman | A61B 1/32 600/222 |
| 9,050,048 B2* | 6/2015 | Nadershahi | A61B 1/32 |
| 2018/0235592 A1* | 8/2018 | Kass | A61B 17/0218 |

FOREIGN PATENT DOCUMENTS

| | | |
|---|---|---|
| CN | 201505126 U | 6/2010 |
| CN | 204468030 U | 7/2015 |
| TW | M331363 U | 5/2008 |

* cited by examiner

*Primary Examiner* — Kevin T Truong
*Assistant Examiner* — Tracy L Kamikawa
(74) *Attorney, Agent, or Firm* — WPAT, PC

(57) ABSTRACT

A vaginal speculum is provided to improve upon the poor convenience of operating the conventional vaginal speculum. The vaginal speculum includes a connecting member having a first end and a second end, and two supporting members. Each of the two supporting members has a coupling end and an insertion end opposite to the coupling end. The coupling ends of the two supporting members respectively connect to the first end and the second end of the connecting member. The two supporting members are configured to be pushed towards or pulled away from each other.

11 Claims, 4 Drawing Sheets

VAGINAL SPECULUM

CROSS REFERENCE TO RELATED APPLICATION

The application claims the benefit of U.S. provisional application No. 62/805,996, filed on Feb. 15, 2019, and the entire contents of which are incorporated herein by reference.

BACKGROUND OF THE INVENTION

1. Field of the Invention

The present invention generally relates to a medical instrument and, more particularly, to a vaginal speculum for gynecological examination purposes.

2. Description of the Related Art

Vaginal speculum is known as duckbill speculum and is one of the most commonly used instruments in gynecological surgeries. Most of the doctors need to use the vaginal speculum to open the vaginal walls for the purposes of examining the condition of the vagina or collecting the secretion using the medical instruments. In this manner, the doctor is able to properly examine the vagina and the organs around the vagina (for example, the cervix) to establish a correct diagnosis.

The conventional vaginal speculum includes a top arm and a bottom arm. Each of the top and bottom arms is designed in a thin fashion. Each of the top and bottom arms includes an expansion end and an engagement end. The engagement end of the top arm is pivotally engaged with the engagement end of the bottom arm. The expansion ends of the top and bottom arms are flat. In addition, the conventional vaginal speculum further includes two handles connecting to the engagement end of the bottom arm and extending away from the top arm. One of the two handles is provided with a through-hole. Another handle includes an abutting portion facing the through-hole. A screw extends through the through-hole and abuts the abutting portion, such that the expansion ends of the top and bottom arms are arranged in an expansion manner with an expansion angle. Then, a nut is threadedly engaged with the screw for examination purposes. An example of such a conventional vaginal speculum is disclosed in Taiwan Patent No. M331363 entitled "vaginal speculum."

At the time the conventional vaginal speculum is manufactured, the nut is loosely fit with the screw in order for the doctor to conveniently operate the nut during the surgery. However, if the nut drops to the ground, the nut should be cleaned and sterilized before it can be attached back to the screw. Furthermore, the expansion angle between the top and the bottom arms should be adjusted as desired before the nut can be fixed in a certain position on the screw. In addition, it is always needed to turn the nut regardless of whether the top and the bottom arms are to be expanded or closed. Therefore, the operation of the conventional vaginal speculum is troublesome and time-consuming, leading to a low operational efficiency of the surgery.

In light of this, it is necessary to improve the conventional vaginal speculum.

SUMMARY OF THE INVENTION

It is therefore the objective of this invention to provide a vaginal speculum which can be operated to smoothly open a vagina, attaining a convenient operation and a high operational efficiency of the surgery.

It is another objective of this invention to provide a vaginal speculum with enhanced convenience in manipulation.

It is a further objective of this invention to provide a vaginal speculum with a reduced cost.

It is yet a further objective of this invention to provide a vaginal speculum with an enhanced structural strength.

In an aspect, a vaginal speculum according to an embodiment of the invention includes a connecting member and two supporting members. The connecting member has a first end and a second end. Each of the two supporting members has a coupling end and an insertion end opposite to the coupling end. The coupling ends of the two supporting members respectively connect to the first end and the second end of the connecting member. The two supporting members are configured to be pushed towards or pulled away from each other. The connecting member is a semi-circle ring body having two distal ends that define end points of a semi-circle shape of the semi-circle ring body. The two distal ends respectively define the first end and the second end. A cross section with the semi-circle shape of the semi-circle ring body lies in a reference plane. In a process that the vaginal speculum is inserted into a vagina of a patient, an inserting direction is defined perpendicular to the reference plane. In an original orientation of the two supporting members before and after insertion into the vagina, the vaginal speculum is configured to form a U-like shape in a view of the vaginal speculum taken in the inserting direction. The two supporting members and the connecting member are integrally formed with each other.

Accordingly, the vaginal speculum according to the present invention provides a convenient use for the doctor operating the vaginal speculum. In either case of opening and closing the vaginal speculum, the doctor does not need to turn the nut as is required by the conventional vaginal speculum. In this regard, the examination time is shortened, leading to a convenient operation and a high operational efficiency of the surgery.

In an example, the connecting member may include a first plate, a second plate and a connecting portion is able to be connected and located between the first plate and the second plate. Thus, the structure is simple for convenient manufacture, reducing the cost.

In the example, the connecting portion may extend from the first end to the second end. Thus, the connecting portion can connect the entire first and second plates, increasing the structural strength of the connecting member.

In the example, the connecting member can be made of elastic material. Thus, the two supporting members can return to the original orientation quickly, leading to an enhanced convenience in manipulation.

In the example, the two supporting members and the connecting member can be integrally formed with each other. Thus, the two supporting members can firmly connect with the connecting member, enhancing the structural strength of the vaginal speculum.

In the example, outer faces of the two supporting members and end faces of the insertion ends may be curved. Thus, the foreign body sensation can be avoided when the two supporting members are positioned in the vagina, providing the patient with comfort during the surgery.

In the example, the connecting member and the two supporting members may be made of lightweight plastic material. The lightweight plastic material includes disposable plastic, biodegradable plastic or sterilizable plastic.

Thus, it prevents the vaginal speculum from sliding out of the vagina under a large weight thereof, so as to enhance the convenience in manipulation.

In the example, the two supporting members both can be 7-8 cm long and 2 cm wide. Thus, according to the dimension, the vaginal speculum can be suitable for most people, leading to an enhanced convenience in manipulation and manufacture.

In the example, a spreading space can be formed between the coupling ends of two supporting members, and can be 4-5 cm. Thus, according to the dimension, the vaginal speculum can be suitable for most people, leading to an enhanced convenience in manipulation and manufacture.

In the example, a force is applied to push the two supporting members towards each other. The insertion ends are configured to be inserted into a vagina of a patient. The two supporting members may return to the original orientation and are configured to open the vagina under a removal of the force. Thus, it provides a convenient use for the doctor operating the vaginal speculum, and shortens the examination time.

In the example, a lateral face of each of the two supporting members can be provided with an anti-slip portion. Thus, the friction between the two supporting members and the vaginal walls is increased, so as to prevent displacement of the two supporting members in the vagina or to prevent the two supporting members from sliding out of the vagina.

In the example, the insertion ends of the two supporting members can be each respectively provided with an outer expansion portion, wherein the outer expansion portions extend away from each other. Thus, the two insertion ends can abut the vagina more securely, so as to prevent displacement of the two supporting members in the vagina or to prevent the two supporting members from sliding out of the vagina.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
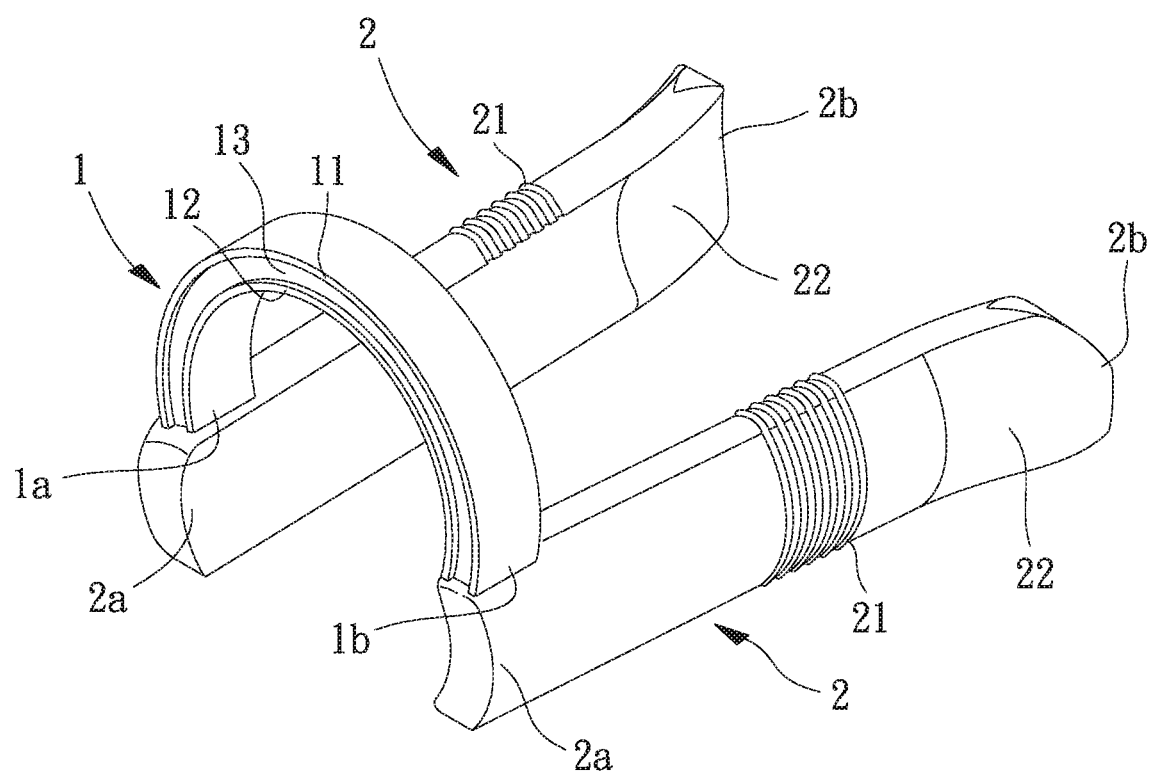
FIG. 1 is a perspective view of a vaginal speculum according to an embodiment of the invention.

In the various figures of the drawings, the same numerals designate the same or similar parts. Furthermore, when the term "inner", "outer" "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

With reference to FIG. 1, a vaginal speculum of a preferred embodiment according to the present invention includes a connecting member 1 and two supporting members 2 connected to the connecting member 1.

The connecting member 1 may be in a curved shape and includes a first end 1a and a second end 1b. The connecting member 1 is preferably made of elastic material in order to return to the original orientation after bending. For example, a force is applied to push the first end 1a and the second end 1b towards each other. When the force is removed, the first end 1a and the second end 1b return to the original orientation.

Additionally, the structure of the connecting member 1 is not limited in the present invention. For example, the connecting member 1 can be a single plate bent into the curved shape. In this embodiment, the connecting member 1 includes a first plate 11, a second plate 12 and a connecting portion 13 connected and located between the first plate 11 and the second plate 12. In this manner, the structure of the connecting member 1 is simple for convenient manufacture. The connecting portion 13 is generally configured to connect the first and second plates 11 and 12 to each other. The connecting portion 13 can connect parts of the first and second plates 11 and 12 to reduce the amount of the material used as well as the cost. In this embodiment, the connecting portion 13 extends from the first end 1a to the second end 1b, such that the connecting portion 13 can connect the entire first and second plates 11 and 12, increasing the structural strength of the connecting member 1.

Figure 2:
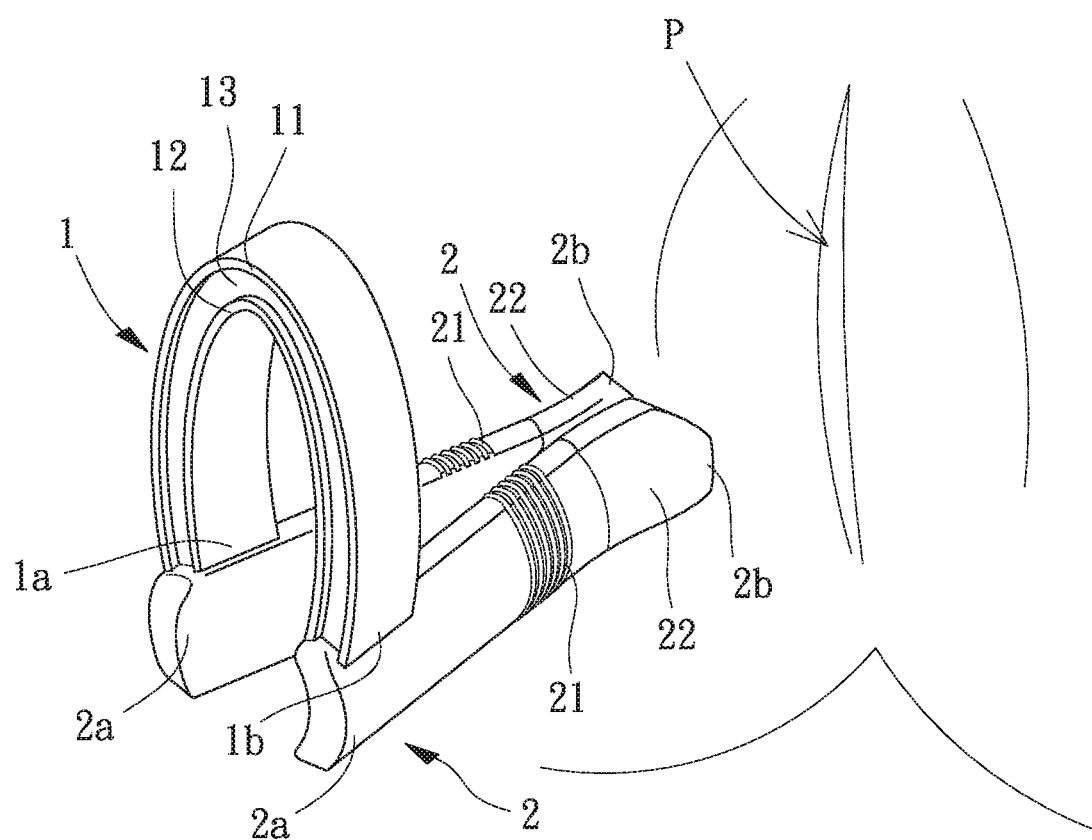
FIG. 2 is a perspective view of the vaginal speculum having two supporting members being pushed towards each other.

With reference to FIGS. 1 and 2, each of the two supporting members 2 includes a coupling end 2a and an insertion end 2b. The coupling ends 2a of the two supporting members 2 are respectively connected to the first and second ends 1a and 1b by ways of adhesion or fusion. The two supporting members 2 and the connecting member 1 are integrally formed with each other in this embodiment to enhance the structural strength of the vaginal speculum. The end face of each insertion ends 2b is preferably curved such that the insertion ends 2b can be inserted into a vagina P of the patient without causing discomfort sensation. Besides, the lateral face 20 of the two supporting members 2 is preferably curved; thus, when the two supporting members 2 are inserted into the vagina P as shown in FIG. 3, the lateral faces 20 of the two supporting members 2 abut the inner wall of the vagina P to avoid a foreign body sensation in the vagina P.

Figure 3:
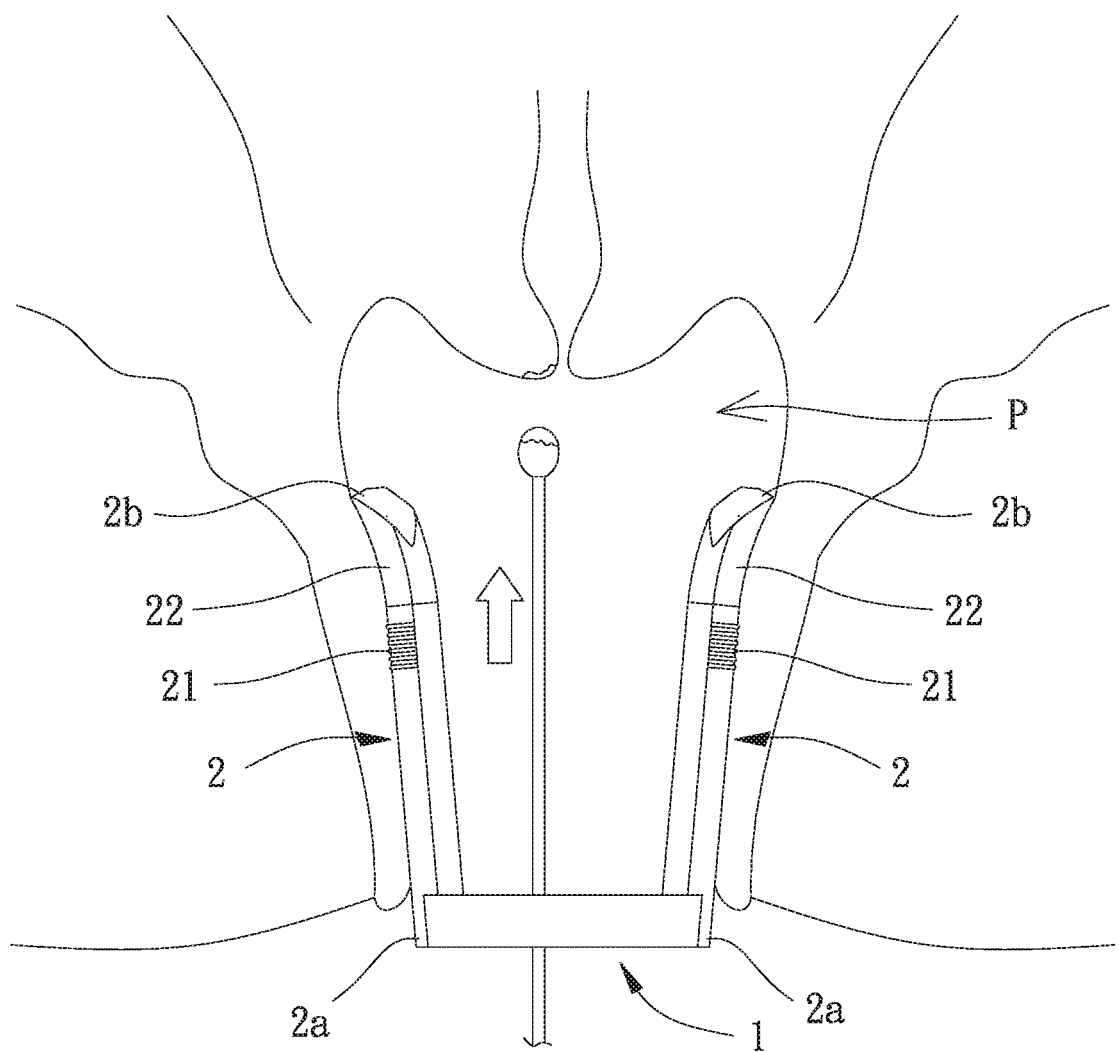
FIG. 3 is an illustrated figure of the vaginal speculum according to the embodiment of the invention in use.

With reference to FIGS. 2 and 3, the lateral face 20 of each of the two supporting members 2 is provided with an anti-slip portion 21 which is designed to increase the friction between the two supporting members 2 and the vaginal P walls and to prevent displacement of the two supporting members 2 in the vagina P or to prevent the two supporting members 2 from sliding out of the vagina P. The structure of the anti-slip portions 21 is neither limited in the present invention nor limited in the drawing. In this embodiment, each of the anti-slip portions 21 of the two supporting members 2 is in the form of a plurality of protruding ribs for discussion purpose. In other embodiment, however, the anti-slip portions 21 can be soft pads, engraved lines, etc. In addition, each of the insertion ends 2b includes an outer expansion portion 22. The outer expansion portions 22 of the two supporting members 2 extend away from each other such that the insertion ends 2b can securely abut the inner wall of the vagina P, further preventing displacement of the two supporting members 2 in the vagina P or preventing the two supporting members 2 from sliding out of the vagina P.

Figure 4:
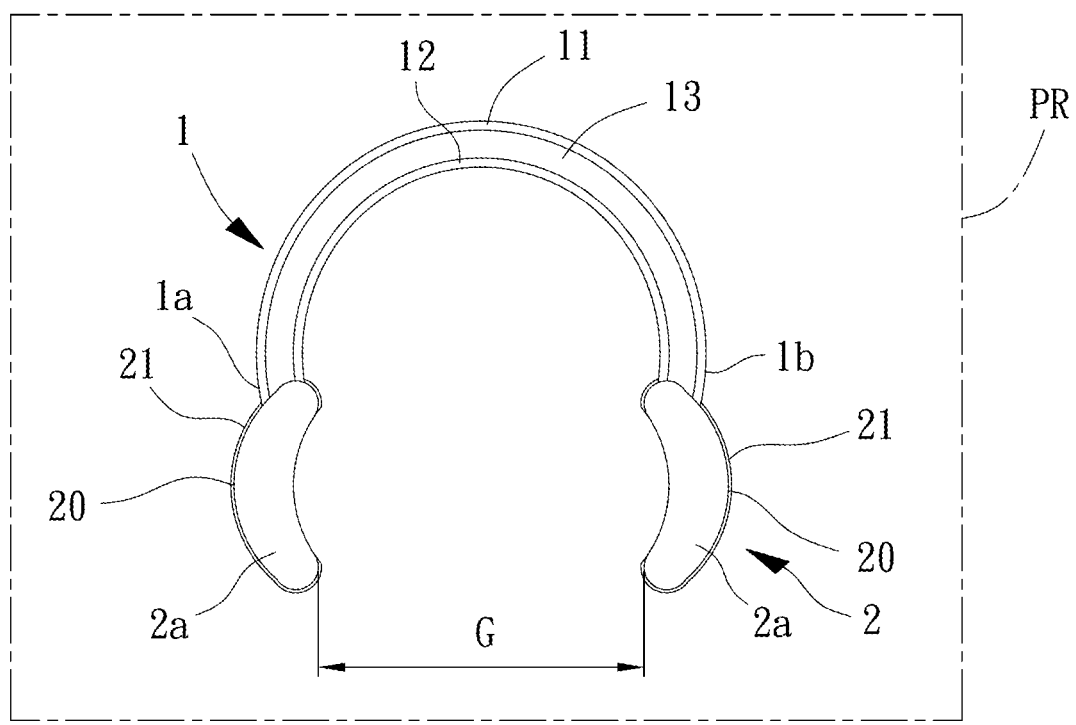
FIG. 4 is a plan view of the vaginal speculum according to the embodiment of the invention.
Figure 5:
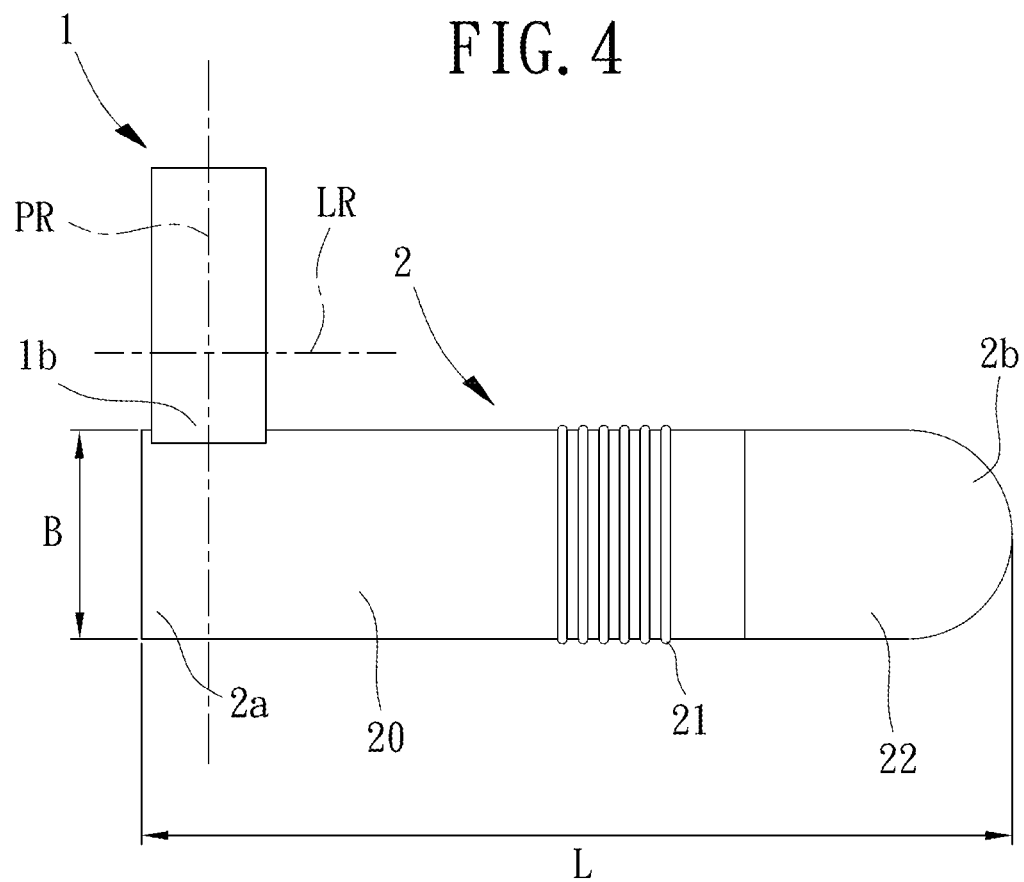
FIG. 5 is a side view of the vaginal speculum according to the embodiment of the invention.

With reference to FIGS. 4 and 5, besides, both the two supporting members 2 are preferably 7-8 cm long and 2 cm wide. Also, a spreading space G can form between the coupling ends 2a of two supporting members 2, and is preferably 4-5 cm. Thus, according to the dimension, the vaginal speculum can be suitable for most people, further enhancing convenience in use and manufacturing. More specifically, the connecting member 1 is a semi-circle ring body having two distal ends that define end points of a semi-circle shape of the semi-circle ring body. The two distal ends respectively define the first end 1a and the second end 1b. A cross section with the semi-circle shape of the semi-circle ring body lies in a reference plane PR. In a process that the vaginal speculum is inserted into the vagina P, an inserting direction is defined perpendicular to the reference plane PR along a reference line LR. In an original orientation of the two supporting members 2 before and after insertion into the vagina P, the vaginal speculum is configured to form a U-like shape in a view of the vaginal speculum taken in the inserting direction. The two supporting members and the connecting member are integrally formed with each other.

It is noted that the vaginal speculum in the present invention can be made of lightweight plastic material such as disposable plastic, biodegradable plastic or sterilizable plastic. This not only provides a hygienic use of the vaginal speculum but also keeps the weight of the vaginal speculum in a certain range to prevent the vaginal speculum from sliding out of the vagina P under a large weight thereof.

With reference to FIGS. 2 and 3, based on the above structure, when the doctor operates the vaginal speculum, the doctor can hold and apply a force to the two supporting members 2 to push the insertion ends 2b towards each other as is shown in FIG. 2. The insertion ends 2b can be inserted into the vagina P of the patient to position the two supporting members 2 in the vagina P. Then, the force can be removed. The two supporting members 2 are pulled away from each other and return to the original orientation under the elasticity of the connecting member 1 to open the vagina P. Therefore, the doctor can smoothly operate the vaginal speculum simply by himself/herself. In either case of opening and closing the vaginal speculum, the doctor does not need to turn the nut as is required by the conventional vaginal speculum. In this regard, the examination time is shortened, leading to a convenient operation and a high operational efficiency of the surgery.

Because the insertion ends 2b are respectively provided with the outer expansion portions 22 and the lateral face 20 of the two supporting members 2 are respectively provided with the anti-slip portions 21, the friction between the two supporting members 2 and the vaginal P walls is increased. This prevents displacement of the two supporting members 2 in the vagina P or prevents the two supporting members 2 from sliding out of the vagina P. In addition, the lateral faces 20 of the two supporting members 2 and the end faces of the insertion ends 2b are curved to avoid discomfort sensation such as foreign body sensation when the two supporting members are inserted into or placed in the vagina, providing the patient with comfort during the surgery.

In view of the foregoing, the vaginal speculum according to the present invention provides a convenient use for the doctor operating the vaginal speculum simply by himself/herself. In either case of opening and closing the vaginal speculum, the doctor does not need to turn the nut as is required by the conventional vaginal speculum. In this regard, the examination time is shortened, leading to a convenient operation and a high operational efficiency of the surgery.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A vaginal speculum comprising:
   a connecting member having a first end and a second end; and
   two supporting members, wherein each of the two supporting members has a coupling end and an insertion end opposite to the coupling end, wherein the coupling ends of the two supporting members respectively connect to the first end and the second end of the connecting member, and the two supporting members are configured to be pushed towards or pulled away from each other;
   wherein the connecting member is a semi-circle ring body having two distal ends that define end points of a semi-circle shape of the semi-circle ring body, the two distal ends respectively define the first end and the second end, a cross section with the semi-circle shape of the semi-circle ring body lies in a reference plane;
   wherein in a process that the vaginal speculum is inserted into a vagina of a patient, an inserting direction is defined perpendicular to the reference plane;
   wherein in an original orientation of the two supporting members before and after insertion into the vagina, the vaginal speculum is configured to form a U-like shape in a view of the vaginal speculum taken in the inserting direction; and
   wherein the two supporting members and the connecting member are integrally formed with each other.

2. The vaginal speculum as claimed in claim 1, wherein the connecting member includes a first plate, a second plate and a connecting portion connected and located between the first plate and the second plate.

3. The vaginal speculum as claimed in claim 2, wherein the connecting portion extends from the first end to the second end.

4. The vaginal speculum as claimed in claim 1, wherein the connecting member is made of elastic material.

5. The vaginal speculum as claimed in claim 1, wherein outer faces of the two supporting members and end faces of the insertion ends are curved.

6. The vaginal speculum as claimed in claim 1, wherein the connecting member and the two supporting members are made of lightweight plastic material, and wherein the lightweight plastic material includes disposable plastic, biodegradable plastic or sterilizable plastic.

7. The vaginal speculum as claimed in claim 1, wherein each of the two supporting members has a length of 7-8 cm and a width of 2 cm.

8. The vaginal speculum as claimed in claim 1, wherein a spreading space forms between the coupling ends of the two supporting members, and wherein the spreading space has a length of 4-5 cm.

9. The vaginal speculum as claimed in claim 1, wherein a force is applied to push the two supporting members towards each other, wherein the insertion ends are configured to be inserted into the vagina, and wherein the two supporting members return to the original orientation and are configured to open the vagina under a removal of the force.

10. The vaginal speculum as claimed in claim 1, wherein an outer side of each of the two supporting members is provided with an anti-slip portion.

11. The vaginal speculum as claimed in claim 1, wherein the insertion ends of the two supporting members each are respectively provided with an outer expansion portion, wherein the outer expansion portions extend away from each other.

* * * * *